US012600938B2

(12) United States Patent
Egaña-Erazo et al.

(10) Patent No.: US 12,600,938 B2
(45) Date of Patent: Apr. 14, 2026

(54) METHODS FOR PRESERVATION OF PHOTOSYNTHETICALLY ACTIVE CELLS AND PHOTOSYNTHETIC BIOMATERIALS

(71) Applicant: SYMBIOX, INC., San Diego, CA (US)

(72) Inventors: Jose-Tomás Egaña-Erazo, Santiago (CL); Rocio Corrales-Orovio, Santiago (CL)

(73) Assignee: SYMBIOX, INC., San Diego, CA (US)

( * ) Notice: Subject to any disclaimer, the term of this patent is extended or adjusted under 35 U.S.C. 154(b) by 85 days.

(21) Appl. No.: 18/033,762

(22) PCT Filed: Oct. 28, 2021

(86) PCT No.: PCT/US2021/057139
§ 371 (c)(1),
(2) Date: Apr. 25, 2023

(87) PCT Pub. No.: WO2022/094143
PCT Pub. Date: May 5, 2022

(65) Prior Publication Data

US 2023/0407236 A1     Dec. 21, 2023

Related U.S. Application Data

(60) Provisional application No. 63/107,370, filed on Oct. 29, 2020.

(51) Int. Cl.
*C12N 1/12*     (2006.01)
(52) U.S. Cl.
CPC ..................................... *C12N 1/12* (2013.01)
(58) Field of Classification Search
CPC ....................................................... C12N 1/12
See application file for complete search history.

(56) References Cited

U.S. PATENT DOCUMENTS

| | | | |
|---|---|---|---|
| 9,144,589 B2 * | 9/2015 | Eagana-Erazo | C12N 1/12 |
| 2010/0287669 A1 | 11/2010 | Bate et al. | |
| 2013/0217083 A1 * | 8/2013 | VanWinkle-Swift | C12P 7/64 |
| | | | 435/134 |
| 2016/0015761 A1 | 1/2016 | Egana-Erazo et al. | |

FOREIGN PATENT DOCUMENTS

| | | |
|---|---|---|
| EP | 3090626 A1 | 11/2016 |
| JP | 2006288221 A | 10/2006 |
| WO | WO2011/116936 A1 * | 9/2011 |

OTHER PUBLICATIONS

Bold's Basal Medium; https://propagate.one/bolds-basal-medium-bbm/?print=print (Year: 2025).*

International Preliminary Report on Patentability for PCT App No. PCT/US2021/057139 mailed May 11, 2023, 7 pgs.

International Search Report and Written Opinion for PCT/US2021/057139 dated Feb. 23, 2022, 8 pages.

Camacho-Rodriguez, J., et al. "Long-term preservation of concentrated Nannochloropsis gaditana cultures for use in aquaculture." Journal of Applied Phycology, 2015, DOI: 10.1007/s10811-015-0572-y.

Scarbough, Chasity et al., "Comparative analysis of cryopreservation methods in Chlamydomonas reinhardtii." Cryobiology, 2016, vol. 73. pp. 291-295.

Extended European Search Report for EP App No. 21887563.1, dated Aug. 7, 2024, 10 pgs.

Chen, S., et al., In-situ-sprayed therapeutic hydrogel for oxygen-actuated Janus regulation of postsurgical tumor recurrence/metastasis and wound healing, Nature Communications, 15, 814 (2024). https://doi.org/10.1038/s41467-024-45072-x, pp. 1-17.

He, Y., et al., Oxygen-releasing biomaterials for chronic wounds breathing: From theoretical mechanism to application prospect, Materials Today Bio, 20, 2023, 15 pgs.

* cited by examiner

*Primary Examiner* — Brian Gangle
*Assistant Examiner* — Lakia J Jackson-Tongue
(74) *Attorney, Agent, or Firm* — Buchalter LLP

(57)     ABSTRACT

Methods of storage and preservation of photosynthetically active cells and photosynthetic biomaterials are provided herein. Contemplated methods comprise storing the cells and biomaterials at a refrigeration temperature, optionally without light. The stored cells and biomaterials may be placed in a nitrogen containing medium under illumination before use. The chlorophyll content, oxygen consumption rate, oxygen production rate and/or morphology may be substantially preserved throughout the storage and awakening process.

5 Claims, 4 Drawing Sheets

METHODS FOR PRESERVATION OF PHOTOSYNTHETICALLY ACTIVE CELLS AND PHOTOSYNTHETIC BIOMATERIALS

CROSS-REFERENCE TO RELATED APPLICATIONS

This application is US National Stage entry of International Patent Application PCT/US2021/057139, filed Oct. 28, 2021, which claims benefit of priority from Provisional Patent Application 63/107,370, filed Oct. 29, 2020, the contents of both of which are incorporated herein by reference.

FIELD OF THE INVENTION

The field of the invention is storage and preservation of photosynthetically active cells and photosynthetic biomaterials.

BACKGROUND

Insufficient oxygen supply represents a large clinical issue in several fields of human physiology and medicine. It has been suggested that the implantation of photosynthetic cells could provide oxygen to tissues even in the absence of a vascular supply. Exemplary photosynthetic biomaterials (e.g., scaffolds), photosynthetic cellular substances and methods of use are described in U.S. patent application Ser. No. 15/845,016, filed on Dec. 18, 2017, and Ser. No. 14/845,063, filed on Sep. 3, 2015. These and all other extrinsic materials discussed herein are incorporated by reference in their entirety. Where a definition or use of a term in an incorporated reference is inconsistent or contrary to the definition of that term provided herein, the definition of that term provided herein applies and the definition of the term in the reference does not apply.

Unfortunately, the intrinsic low half-life of seeded photosynthetic cells is viewed as severely limiting the potential use of such cells and photosynthetic biomaterials.

The present disclosure is directed toward one or more improved features identified below, and to methods that address the above-mentioned problems.

SUMMARY

The inventive subject matter comprises methods for preserving photosynthetically active cells for later use. Contemplated methods can comprise the step of storing photosynthetically active cells a temperature range between 1-5° C., optionally without light. In some aspects, the step of storing photosynthetically active cells a temperature range between 1-5° C. without light is for a period of at least 3 weeks, at least 4 weeks, at least 6 weeks, or at least 8 weeks. The period may be continuous, or in some embodiments, may not be entirely continuous. For example, a step of storing photosynthetically active cells at a temperature range between 1-5° C. without light for a period of at least 4 weeks can be completed within 4 weeks and 1 day, within 4 weeks and 2 days, within 4 and a half weeks, within 5 weeks, within 5 and a half weeks, or within 6 weeks. In some aspects, the step of storing can comprise storing the cells in a medium that lacks nitrogen. It should be appreciated that in some aspects the step of storing photosynthetically active cells can occur at some temperatures outside of the 1-5° C. range. For example, it is contemplated that storing the cells at up to 6° C. may be suitable while preserving the cells for a period of at least 3 weeks, at least 4 weeks, at least 6 weeks, or at least 8 weeks. However, the ability to preserve the cells can decrease with an increase in temperature.

A subsequent step may comprise suspending the photosynthetically active cells in a nitrogen-containing medium (e.g., TAP). The suspending the cells in the nitrogen-containing medium can be under illumination, for example, under constant illumination for a period of at least one day, at least two days, at least three days, between 1-5 days, between 2-4 days, or between 3-5 days after placing the photosynthetically after cells in the medium comprising nitrogen. In some aspects, suspending the cells in the nitrogen-containing medium can be under different illumination settings, including one or more of on/off cycles of illumination, variations in light intensity, and variations in the illumination source. In some aspects, a step of illuminating can occur after the step of suspending the photosynthetically active cells in the nitrogen-containing medium, for example, after reaching a temperature higher than the storage temperature (e.g., room temperature) or after acclimating to room temperature. It is contemplated a chlorophyll content of the photosynthetically active cells after storing and suspending can be preserved to be at least 80%, at least 85%, or more preferably at least 90% of the chlorophyll content of the photosynthetically active cells before storing and suspending. Additionally or alternatively, an oxygen consumption rate of the photosynthetically active cells after storing and suspending is at least 80%, at least 85%, and more preferably at least 90% of the oxygen consumption rate of the photosynthetically active cells before storing and suspending. Additionally or alternatively, an oxygen production rate of the photosynthetically active cells after storing and suspending is at least 80%, at least 85%, and more preferably at least 90% of the oxygen production rate of the photosynthetically active cells before storing and suspending. The preserved photosynthetically active cells may compose a photosynthetic biomaterial.

The inventive subject matter further comprises a preserved photosynthetic scaffold, comprising photosynthetically active cells seeded onto a biomaterial, wherein the photosynthetically active cells have been stored at temperatures between 1-5° C. for a period of at least 4 weeks, optionally in a medium lacking nitrogen, and optionally without light and subsequently suspended in a nitrogen-containing medium under illumination (e.g., for a period of at least 1 day, at least 2 days, at least 3 days, between 3-5 days, between 1-5 days, or at least 4 days). The photosynthetically active cells can be seeded onto the biomaterial before, during or after being stored and subsequently suspended or woken up.

The inventive subject matter further comprises photosynthetically active cells in at least one of a liquid, gel and cream, wherein the photosynthetically active cells have been stored at temperatures between 1-5° C. for a period of at least 4 weeks, optionally in a medium lacking nitrogen, and optionally without light and subsequently suspended in a nitrogen-containing medium under illumination (e.g., for a period of at least 1 day, at least 2 days, at least 3 days, between 3-5 days, between 1-5 days, or at least 4 days).

Other advantages and benefits of the disclosed compositions and methods will be apparent to one of ordinary skill with a review of the following drawings and detailed description.

BRIEF DESCRIPTION OF THE DRAWINGS

The structure and operation of the present invention will be understood from a review of the following detailed description and the accompanying drawings in which like reference numerals refer to like parts and in which:

FIG. 1A is a bar graph illustrating the chlorophyll content of *C. reinhardtii* (per pellet) after preservation at room temperature and at 4° C.;

FIG. 1B is a bar graph illustrating the Oxygen consumption rates after preservation at room temperature and at 4° C.;

FIG. 1C is a bar graph illustrating the Oxygen production rates after preservation at room temperature and at 4° C.;

DETAILED DESCRIPTION

Figure 2A:
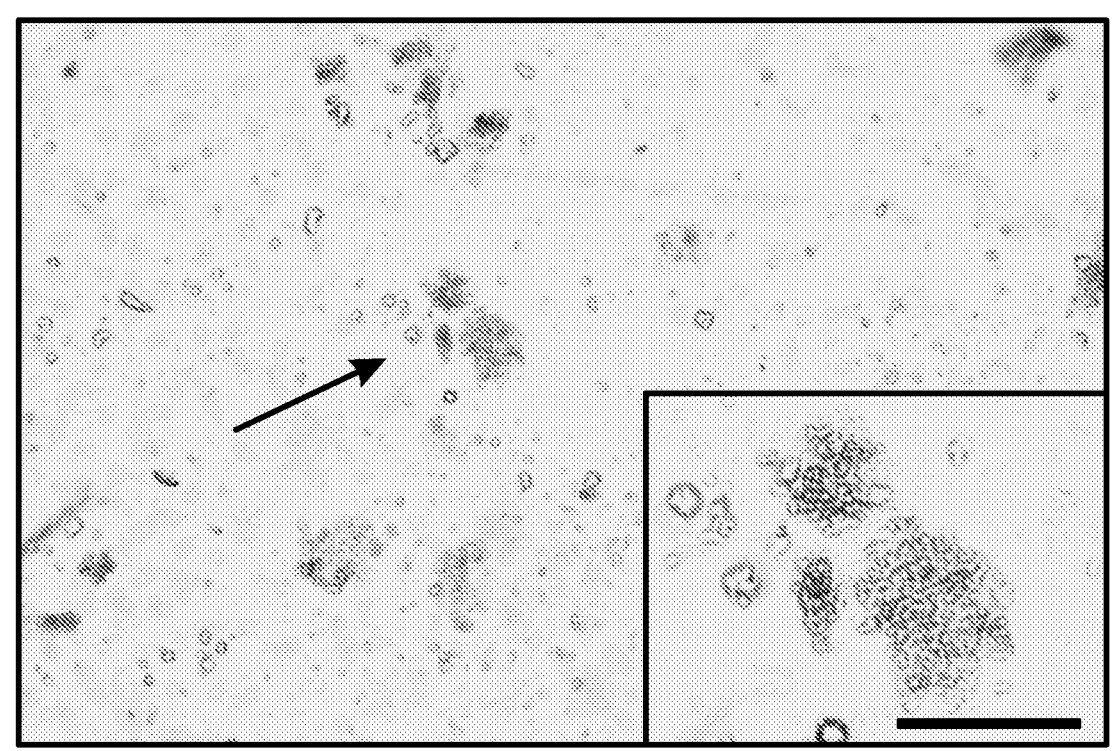
FIG. 2A illustrates morphology of *C. reinhardtii* after preservation at room temperature.

The detailed description, in connection with the accompanying drawings, is intended as a description of various embodiments and is not intended to represent the only embodiments in which the disclosure may be practiced. The detailed description includes specific details for the purpose of providing a thorough understanding of the embodiments. However, it will be apparent that those skilled in the art will be able to understand the disclosure without these specific details.

The present invention is generally directed towards preserving and storing photosynthetic biomaterials and photosynthetically active cells under a hibernation-like state, without substantially negatively affecting their functionality, to increase their shelf life.

As taught in application Ser. Nos. 15/845,016 and 14/845,063, photosynthetic cells may be seeded in scaffolds mimicking features of the extracellular matrix and providing a structure that serves as a guide for growth of new tissue. The term "photosynthetic cells" or "photosynthetically active cells" as used in the present application shall comprise cells and cell organisms that are photosynthetically active, e.g., photosynthetic cells as well as isolated chloroplasts as long as they release oxygen. The term "scaffold" when used in the present application refers to a structure or carrier matrix to which cells can attach or on which cells can proliferate. For example, the term "scaffold" should be interpreted to include biomaterials such as sutures, bandages, mesh, bioartificial 3D scaffolds (e.g., 3D gelatin scaffolds), decellularized tissues, and wound dressing, which may be used as delivery vehicles for the photosynthetic cells. The scaffold can comprise one or more natural (e.g., collagen, fibrin, chitosan, glycosaminoglycans) or synthetic (e.g., polylactic acid, polyglycolic acid, polycaprolactone) materials, may be biodegradable or non-biodegradable, and may be synthesized using any suitable method(s). After implantation of the cells, for example, with the biomaterials, its biocompatible network can provide the structural support for resident cell infiltration and vascularization, which can be followed by the gradual biodegradation of the scaffold, being at the same rate replaced by the formation of new native extracellular matrix (ECM), ensuring proper regeneration of the tissue. The term "tissue" as used in the present application shall refer to any type of tissue in a mammalian organism, and particularly to dermal, bone, nerve, cartilage and blood tissue. Biomaterials loaded with photosynthetic materials and implanted show high biocompatibility in vitro and in vivo.

Preserving photosynthetic cells and biomaterials as described herein could have a tremendous impact in the clinical translation of this approach, as well as to reduce manufacturing times and costs, enabling mass production and particularly increasing their shelf life. Applicant surprisingly discovered that photosynthetic biomaterials can be preserved under hibernation-like conditions while maintaining their complete or substantially complete functionality.

Investigation of Hibernation of Photosynthetic Cells

The standard protocol for the culture of *C. reinhardtii* includes the use of TAP medium (containing nitrogen), exposure to light cycles and room temperature. To investigate hibernation of the photosynthetic cells, microalgae was pelleted by centrifugation and further stored at 4° C. without TAP nor light as described above. At different time points, samples were taken and "woken up" in standard culture conditions as described above. Viability, morphology and metabolic profile or functionality of microalgae were studied at the different times. Specifically, cell viability was assessed by flow cytometry, staining *Chlamydomonas Reinhardtii* with Fluorescein Diacetate (FDA). In parallel, chlorophyll content was quantified by DMSO extraction protocols known in the art. Metabolic activity or functionality of microalgae was studied by quantifying oxygen consumption and production from all samples using Oxygraph+System, Hansatech Instruments. Cell counting was performed to observe cell proliferation of microalgae at each time point. Cell morphology was tested by imaging samples with the use of an inverted fluorescent microscope in order to observe cell morphology along the different time points.

Methods of Preserving Photosynthetic Cells

Microalgae culture and pellet formation: *Chlamydomonas reinhardtii* (UVM4 strain) were grown in sterile liquid TAP medium (Tris-Acetate-Phosphate). For light stimulation, a lamp with the full spectrum of white light was used to provide continuous light exposure (2500 lux, eq. 72.5 μE/m2s1). Once reached exponential growth phase, microalgae were centrifuged at 2000 rpm for minutes. Microalgae were washed by resuspending the pellet in TAP at a concentration of $10^7$ microalgae/mL, and solution was aliquoted in 1.5 mL microtubes containing 1 mL each. Microtubes were then centrifuged at 2000 rpm for 5 minutes. Supernatant was discarded, obtaining pellets containing $10^7$ microalgae.

Microalgae hibernation: Pellets containing $10^7$ microalgae were stored at 4° C. or room temperature, without TAP nor light. Before storage, pellets were resuspended in 1 mL of TAP and chlorophyll content as well as oxygen consumption/production rated were quantified (week 0). At different time points (2, 4, 6 and 8 weeks) microalgae were "woken up" by resuspending pellet in 1 mL of TAP medium and incubating them for up to 4 days at room temperature with constant illumination, provided by a lamp with the full spectrum of white light.

Figures 1A, 1B, 1C:
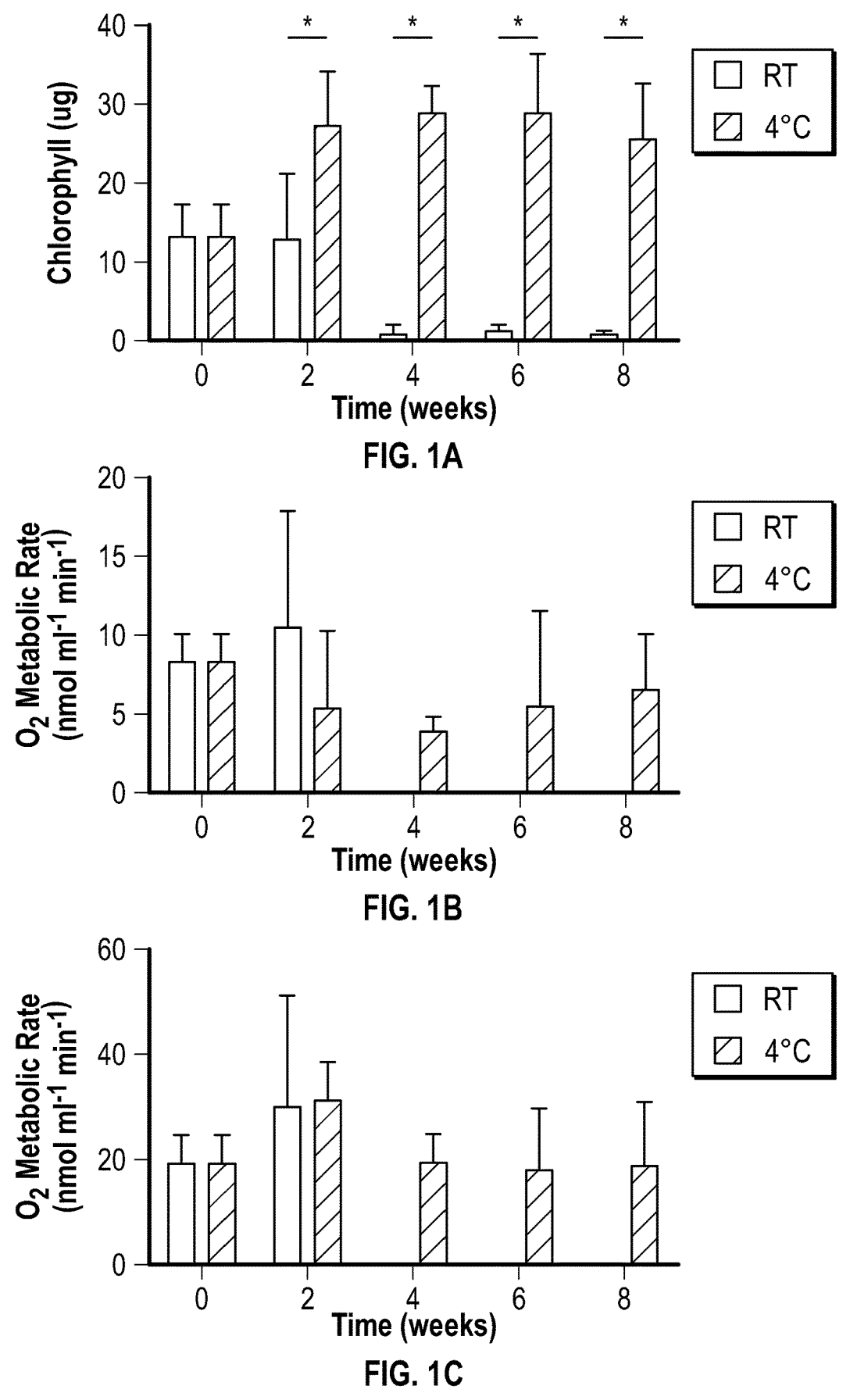

After the waking up process, chlorophyll content and oxygen consumption/production rates were quantified, for both pellets incubated at room temperature and at 4° C. FIGS. 1A-1C illustrate functionality of *C. reinhardtii* after preservation at room temperature and at 4° C. Chlorophyll content per pellet (as shown in FIG. 1A), Oxygen consumption rates (as shown in FIG. 1B) and Oxygen production rates (as shown in FIG. 1C) of microalgae are shown, after 0, 2, 4, 6 and 8 weeks post preservation. Storage was performed at room temperature and 4° C. Functionality of *C. reinhardtii* was lost with room temperature storage, especially after the 2 week time period, while functionality was maintained at 4° C. The data in FIGS. 1A-1C is represented as mean+SD.

Figure 2B:
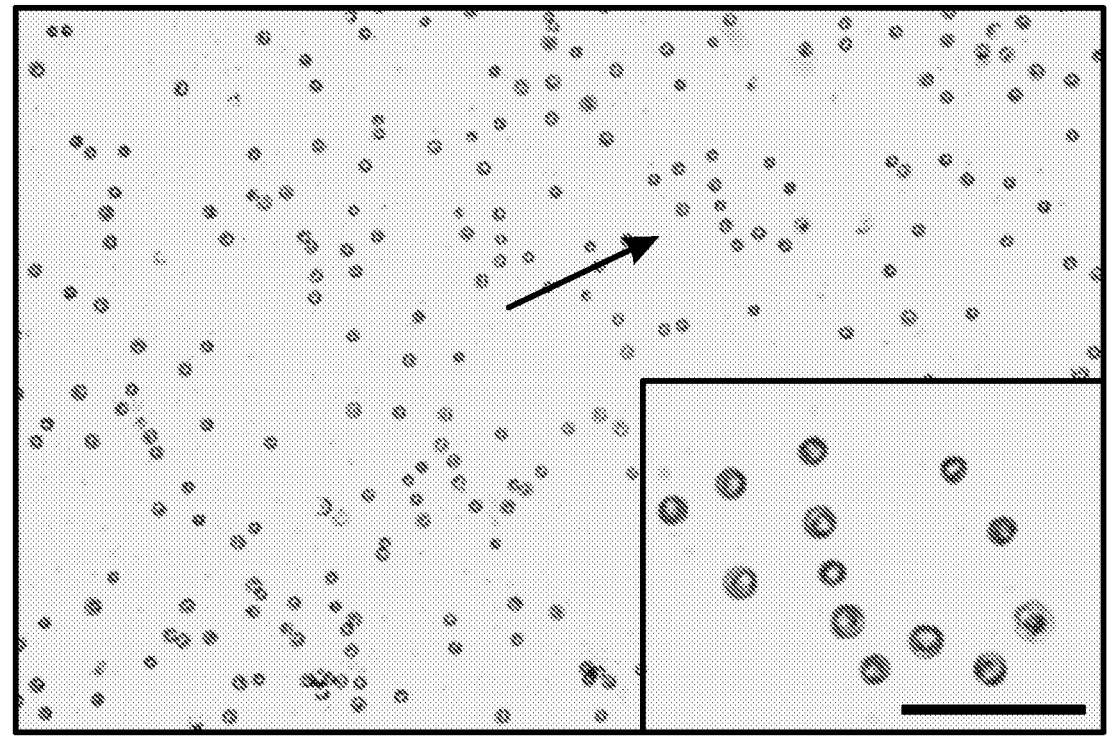
FIG. 2B illustrates morphology of *C. reinhardtii* after preservation at 4° C.

Additionally, *C. reinhardtii* were imaged microscopically after 4 weeks of preservation, to observe microalgae morphology and integrity after preservation at room temperature and at 4° C. as shown in FIGS. 2A-2B. The morphology of *C. reinhardtii* observed under light microscopy with magnification after 4 weeks preservation at room temperature (as shown in FIG. 2A) versus the morphology of *C. reinhardtii* observed under light microscopy with 20× magnification after 4 weeks preservation at 4° C. (as shown in FIG. 2B) illustrate that the morphology of the microalgae preserved at room temperature is completely lost, while standard morphology is observed in microalgae stored at 4° C. after 4 weeks. The inserts in FIGS. 2A and 2B show magnification of the image at the area indicated by the arrows. Scale bars represent 50 μm.

Results—8 Weeks

These results showed the importance of cryopreserving the microalgae in preserving the morphology and functionality of microalgae. Storage at room temperature results in loss of the morphology and functionality of microalgae, while storage at 4° C. results in preservation or morphology and functionality of microalgae.

Although the investigation relates primarily to preservation of *C. reinhardtii*, it is contemplated that the methods described herein may be used to preserve other photosynthetic cells. The photosynthetic cells used according to the present invention are cells from the genus *Chlamydomonas*, which can grow and maintain photosynthetic activity thereby delivering oxygen after seeding in the scaffolds. *Chlamydomonas* are unicellular green algae with a prominent chloroplast and cilia that lives normally in soil, lakes and streams. *Chlamydomonas* are particularly useful as photosynthetic organism because they are generally regarded as safe (GRAS) with no known viral or bacterial pathogen, and are deemed to lack bacterial endotoxin contamination. Moreover, it is a well-known organism which has been widely used for genetic studies and much is known about its biology, including the entire genome. Furthermore, *Chlamydomonas* can be used under good manufacturing practice (GMP) conditions. As soon as it is no longer needed it can be easily eliminated from the host by light deprivation. *Chlamydomonas* can be transformed by known methods and, thus, can be modified to provide useful properties including the secretion of functional recombinant human proteins.

Investigation of Hibernating Photosynthetic Scaffolds

Photosynthetic scaffolds have been described in Applicant's U.S. patent application Ser. No. 15/845,016, filed on Dec. 18, 2017, and Ser. No. 14/845,063, filed on Sep. 3, 2015. As taught in those applications, photosynthetic cells may be seeded in scaffolds mimicking features of the extracellular matrix and providing a structure that serves as a guide for growth of new tissue. Biomaterials loaded with photosynthetic materials and implanted have shown high biocompatibility in vitro and in vivo.

*C. reinhardtii* was seeded onto different biomaterials, including dermal matrices and surgical sutures, and were preserved for months following the protocols set forth herein to study the effect of the incorporation of a 3-dimensional scaffold in the hibernation-like process. Cell viability and morphology in 3-dimensional scaffolds were assessed along the preservation time. RT-PCR analysis was performed to detect microalgae mRNA in stored biomaterials, evaluating viability of *C. reinhardtii* over time. Chlorophyll content was quantified by DMSO extraction protocol, and preserved biomaterials was plated on TAP agar plates, evaluating growth of microalgae. Photosynthetic biomaterials were imaged by confocal microscopy in order to observe microalgae distribution and morphology. Microalgae Live/Dead staining was performed and observed by confocal imaging to further corroborate the cell viability assays.

Further, metabolic profile and overall functionality and integrity of the preserved photosynthetic biomaterials were characterized by studying the oxygen consumption and production rates (via Oxygraph+system, Hansatech Instruments), microalgae growth factor release by ELISA quantification, characterization of the mechanical properties of biomaterials by rheology/tensile tests, microscopic imaging of the samples by scanning electron microscopy (SEM) to study biomaterial integrity and structure, as well as microalgae distribution and morphology, and macroscopic imaging with the use of lens to observe the overall integrity of the samples.

Methods of Preserving Photosynthetic Biomaterials

Photosynthetic biomaterial fabrication: *Chlamydomonas reinhardtii* (UVM4 strain) were encapsulated in Integra Matrix using fibrin glue, as previously described. See Schenck, T. L. et al. Photosynthetic biomaterials: a pathway towards autotrophic tissue engineering. Acta Biomater. 15, 39-47 (2015). Briefly, Integra Dermal Regeneration Template (Integra®, Integra Life Science Corporation) was used as scaffold, and *C. reinhardtii* were seeded at a concentration of $10^7$ cells/cm2. To do so, microalgae were resuspended in TAP, and mixed in a 1:1 ratio with human fibrinogen (EVICEL®, Johnson & Johnson). Before cell seeding, scaffolds were slightly dried on a sterile gauze, and placed silicone-face down on a sterile cell culture plate. Next, the microalgae-fibrinogen solution was homogeneously added to the scaffolds, followed by the addition of Thrombin (EVICEL®, Johnson & Johnson). Matrices were left undisturbed for 1 h to ensure complete polymerization.

Photosynthetic biomaterial hibernation: Biomaterials were sealed in culture plates and stored at 4° C., without TAP nor light. Before storage, chlorophyll content was quantified, and oxygen consumption/production rates were measured (week 0). At different time points (2, 4 and 6 weeks) matrices were "woken up" by adding TAP medium and incubating them for up to 4 days at room temperature with constant illumination, provided by a lamp with the full spectrum of white light.

Results—6 Weeks

Figures 3A, 3B, 3C:
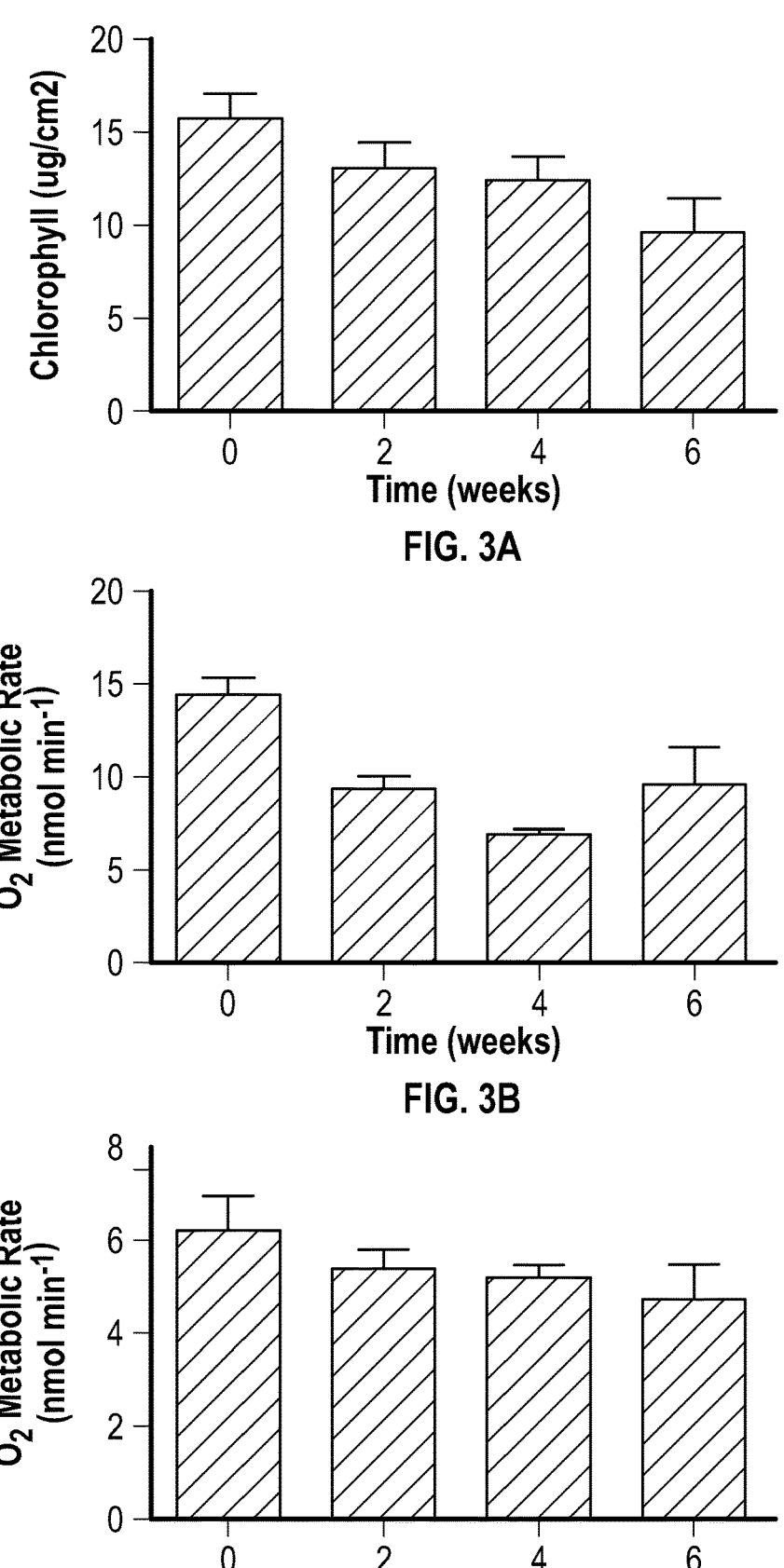
FIG. 3A-3C are bar graphs illustrating the functionality of photosynthetic matrices for dermal regeneration after a hibernation process, with FIG. 3A illustrating chlorophyll content, FIG. 3B illustrating Oxygen consumption rates, and FIG. 3C illustrating Oxygen production rates of the photosynthetic matrices.

Photosynthetic biomaterials comprising *C. reinhardtii* were preliminarily preserved for 6 weeks at 4° C., without TAP nor light. After the waking up process, chlorophyll content and oxygen consumption/production rates were quantified (as shown in FIGS. 3A-3C). Functionality of photosynthetic matrices for dermal regeneration after 0, 2, 4 and 6 weeks of storage under hibernation conditions is illustrated in bar graphs showing: Chlorophyll content (as shown in FIG. 3A), Oxygen production rates (as shown in FIG. 3B) and Oxygen consumption rates (as shown in FIG. 3C) of the photosynthetic biomaterials/matrices. Functionality of the photosynthetic biomaterials/matrices is maintained after storage and recovery. Data represented as mean+SD.

Figure 4:
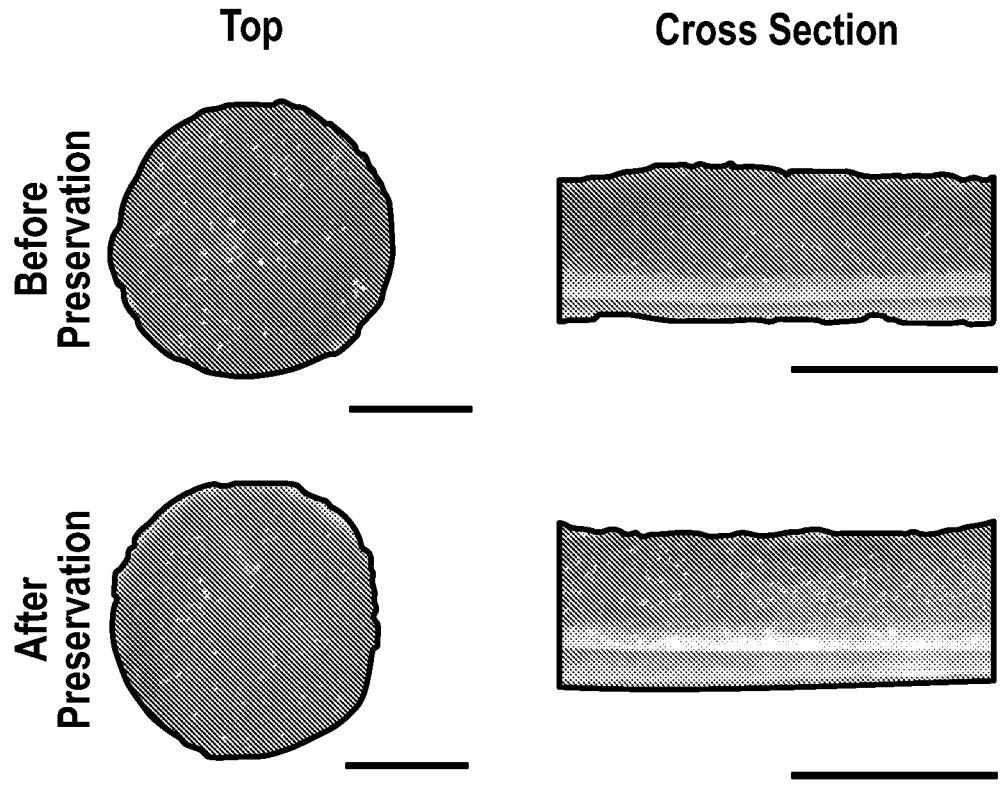
FIG. 4 illustrates the distribution of microalgae before and after preservation of photosynthetic biomaterial.

Additionally, photosynthetic biomaterials were imaged macroscopically, to observe microalgae distribution and biomaterial integrity (as shown in FIG. 4). Macroscopic imaging of photosynthetic matrices for dermal regeneration show a biopsy of photosynthetic matrices before (upper row) and after 6 weeks of preservation (lower row), from a top and cross-sectional view. The images show a homogeneous color and distribution of microalgae before and after preservation. Scale bars represent 5 mm.

The photosynthetic biomaterials of the present invention can comprise the photosynthetic cells and/or chloroplasts in their natural form. It is also possible, particularly to avoid immunological reactions, to protect the cells or isolated chloroplasts by encapsulation with a permeable immunologically inert material, and preserved using the methods as described herein. Such materials and methods for encapsulation are well known in the art and the known methods and materials can be used for the present invention. Examples for a permeable immunologically inert material are natural or synthetic polymers that are physiologically acceptable, i.e. do not interfere with the growth of the tissue and do not disturb the viability of the cells and/or chloroplasts. Examples are hydrogels or alginate. Moreover, it is possible by encapsulation to modify the activity of the photosynthetic cells and/or chloroplasts in the scaffold. For example, by regulating the biodegradability or transparency it is possible to enhance or decrease the activity of the cells and/or chloroplasts and, thereby, to regulate the level of oxygen production.

Methods for genetically engineering photosynthetic cells, like *Chlamydomonas*, are known in the art. Therefore, in some embodiments, the photosynthetic biomaterials may comprise photosynthetic cells that have been genetically engineered to contain nucleic acids encoding for at least one bioactive molecule, such as cytokines, growth factors or angiogenesis factors, or drugs for treating inflammation and/or infections, for example at least one pro-angiogenic growth factor, such as VEGF and bFGF and/or at least one antibacterial or antiviral drug and/or at least one anti-inflammatory agent, and preserved using the methods as described herein. This type of biomaterial may be particularly suited for use for treatment or prevention of inflammation and/or for treatment of injuries and damages, particularly injuries and damages of tissue like skin, nerve, bone, cartilage, and blood tissue, particularly dermal tissue, nerve tissue or bone tissue. The biomaterials may be used for treatment of non-healing wounds and/or chronic wounds and/or massive wounds.

A further advantage by using at least some genetically engineered photosynthetic cells is the continuous delivery of these factors which avoids regular dosing. Furthermore, other useful or helpful proteins can be delivered additionally, for example growth factors and/or drugs. Drugs that are useful in this regard are for example anti-inflammatory agents, anti-viral agents and/or antibiotics that prevent or decrease inflammation and/or infection that easily occur on open wounds, particularly on chronic wounds. Furthermore, anti-scar agents can also be useful. Thereby the growth of the tissue is improved and at the same time the quality of the newly built tissue is also enhanced.

Methods of Preserving Scaffolds with Genetically Modified Photosynthetic Microalgae

*Chlamydomonas reinhardtii* (UVM4 strain) genetically modified to produce recombinant vascular endothelial growth factor (VEGF) were encapsulated in Integra Matrix using fibrin glue, as previously described. See Chávez M N, Schenck T L, Hopfner U, Centeno-Cerdas C, Somlai- Schweiger I, Schwarze C, Machens H G, Heikenwalder M, Bono M R, Allende M L, Nickelsen J, Egaña J T. Towards Autotrophic Tissue Engineering: Photosynthetic Gene Therapy for Regeneration. Biomaterials. 2016; 75:25-36. Briefly, Integra Dermal Regeneration Template (Integra®, Integra Life Science Corporation) was used as scaffold, and the genetically modified UVM4 strain of *C. reinhardtii* were seeded at a concentration of $10^7$ cells/cm2. To do so, microalgae were resuspended in TAP, and mixed in a 1:1 ratio with human fibrinogen (EVICEL®, Johnson & Johnson). Before cell seeding, scaffolds were slightly dried on a sterile gauze, and placed silicone-face down on a sterile cell culture plate. Next, the microalgae-fibrinogen solution was homogeneously added to the scaffolds, followed by the addition of Thrombin (EVICEL®, Johnson & Johnson). Matrices were left undisturbed for 1 h to ensure complete polymerization.

Figure 5:
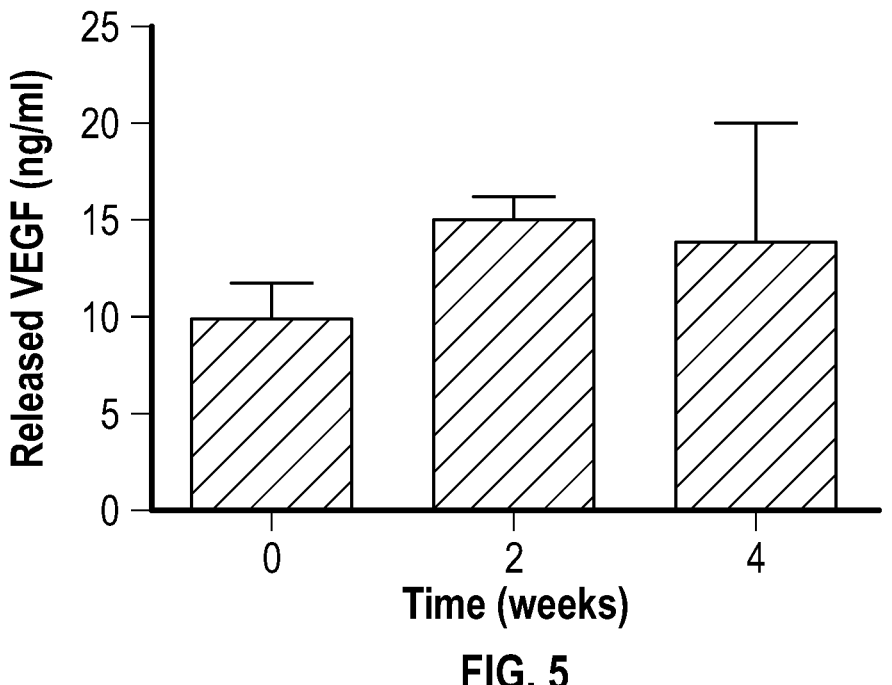
FIG. 5 is a bar graph illustrating the ability to release VEGF at different time points.

The seeded scaffolds were sealed in culture plates and stored at 4° C., without TAP nor light. Before storage, their ability to release VEGF was quantified (week 0). At different time points (2 and 4 weeks) the seeded scaffolds were "woken up" by adding TAP medium and incubating them for up to 4 days at room temperature with constant illumination, provided by a lamp with the full spectrum of white light. Their ability to release VEGF after storage was studied and compared to week 0, as shown in FIG. 5. VEGF release was observed for at least 4 weeks, without significant changes between different time points. Data represented as mean+ SD.

Thus, in some embodiments, photosynthetic cells used for the photosynthetic biomaterials comprise a mixture of *Chlamydomonas* cells provided with wild-type cells and genetically engineered cells that encode factors, like growth and pro-angiogenic factors, and/or agents like antibacterial or antiviral agents, and preserved using the methods as described herein. This may be particularly useful if large wounds on the surface are treated which are prone to infections by bacteria and/or viruses. Furthermore, *Chlamydomonas* cells can be used alone or in combination with other genetically engineered *Chlamydomonas* cells which code for at least one drug having alleviating, mitigating or restoring activity. A combination of cells encoding different agents or the use of cells encoding more than one factor or agent can be used as desired, and preserved using the methods as described herein.

It is contemplated that the substances can be developed as a standalone liquid, gel or cream, or embedded within a bandage, mesh, surgical suture or other scaffold, and preserved using the methods as described herein.

Moreover, in a further embodiment of the present invention, the cells and/or chloroplasts used for the photosynthetic biomaterial to be preserved can be modified regarding their nutrient requirements or light requirements, and preserved using the methods as described herein. Thereby, the biomaterial can be adapted to the light available and thereby, oxygen release can also be adapted accordingly. Photosynthetic cells and/or isolated chloroplasts that have been adapted as to the light requirements are known in the art. Thus, it is possible in specific cases to adapt algae cells and/or chloroplasts for their light requirements depending on the light available and by adding these adapted cells or chloroplasts the activity and, thereby, the oxygen release can be adapted accordingly.

The scaffold that supports the photosynthetic cells as well as the growing tissue can be any scaffold that is known for use for tissue engineering. Material for producing such scaffolds is well known in the art and it is commonly a biocompatible polymer which can be synthetic or natural or a combination of both. Biocompatible in this regard means any material that is compatible with living cells, tissues, organs, or systems, and poses no risk of injury or toxicity, and is not or hardly rejected by the immune system. In a preferred embodiment, biodegradability, nature and structure of the scaffold can be adapted by methods well known to the skilled artisan. Commonly used materials are natural materials like alginate, chitosan, agarose, gelatine, collagen or kappa-carrageenan, or synthetic products like polylysin, polyvinylalcohol, polyethylene glycol or derivatives thereof or mixtures of these products. Collagen and collagenous material or hyaluronic acid as well as derivatives thereof are particularly useful. Furthermore, hydrogels or webs made from fibers or spider silk can also be used. The material used for the scaffold can be biodegradable, i.e. it is degraded with time. In a preferred embodiment the material has a predetermined biodegradability, i.e. it degrades after and/or within a predetermined time period. In another embodiment polymers can be used for preparing the scaffold, that are inert, i.e. do not react with tissue, photosynthetic cells, body fluids, skin or any drug that might be present, and can be deleted when no longer needed. Moreover, decellularized tissues or organs can also be used as scaffolds. The material and its structure are uncritical as long as photosynthetic cells or isolated chloroplasts can be attached, can proliferate and are able to release oxygen to the surroundings.

The scaffold serving as carrier for the cells can have any form that is useful for supporting cells or tissue respectively. Any form known for tissue engineering is suitable, for example it can be a porous substrate, a network, or a woven or non-woven fabric. Any form is useful as long as both types of cells can grow and receive nutrients and oxygen.

The pore size or mesh size of the scaffold is a property that can have an influence on cell attachment, growth and ingrowth of blood vessels. Research on tissue engineering has shown the optimal properties for such carriers and these are known to the skilled person. Thus, the skilled person can choose the best suited pore size or mesh size based on his knowledge and/or with a few routine tests that are described in the prior art.

In one embodiment of the present invention the carrier is a three-dimensional scaffold as described above. In another embodiment of the present invention the carrier may comprise a fibrin solution which can be applied at the site where the photosynthetic cells shall grow, for example a wound. The fibrin solution may be applied and build a fibrinogen network. The advantage is that on the one hand the photosynthetic cells can be applied, for example by spraying, at the site where the photosynthetic scaffold is necessary. On the other hand, the fibrinogen is gradually destroyed in the body but allows the cells to build a network. As fibrin has adhesive properties a fibrin solution comprising photosynthetic cells can adhere to the tissue where it has been applied and adheres at the surface and creates a network that immobilizes the photosynthetic cells on the surface of the skin or another site in the body. The photosynthetic cells can then grow and at the same time deliver oxygen to their environment and, thereby, can supply oxygen to the defect tissue of the skin or organ they are growing on. The fibrin network is support and nutrient at the same time. A fibrin solution comprising photosynthetic cells can also be used to apply a further layer of cells to an already growing tissue if further oxygen supplying cells are necessary. It is contemplated that a fibrin solution containing the photosynthetic cells may be preserved using the methods described herein.

In another embodiment the photosynthetic biomaterial is in the form of a wound dressing or a surgical suture. The carrier for the wound dressing is made from a biocompatible material, that preferably is permeable or semi-permeable. In a preferred embodiment the support layer of the wound dressing is a membrane that is semi-permeable for oxygen. An example for such material is silicone. In another embodiment the support layer is made from a membrane that is permeable for gas to allow gas exchange. The photosynthetic cells in this embodiment are attached to the support layer and, thus, can easily be removed when they are no longer necessary for providing oxygen.

The preserved photosynthetic biomaterials of the present invention may be used to grow and support tissue, preferably tissue like skin, nerve, bone, cartilage, and blood tissue, particularly dermal tissue, nerve tissue or bone tissue, in other words tissue to regenerate or to repair damaged or injured parts of the body. The preserved biomaterials of the present invention can be directly applied to an injured site and allows growing of tissue on-site and thereby supports and particularly provides oxygen for the growing cells.

The preserved photosynthetic biomaterials of the present invention as claimed and described in this specification and all the embodiments thereof, as claimed and described, can be used for treatment of wounds or injuries, particularly for the treatment of damaged or injured tissue like skin, nerve, bone, cartilage, and blood tissue, particularly dermal tissue, nerve tissue or bone tissue. The advantage of being able to preserve such photosynthetic cells and/or biomaterials for extended periods of time can account for the severely limiting potential use of such cells and biomaterials that has been experienced due to the intrinsic low half-life of seeded photosynthetic cells.

Moreover, it has been found that instead of or additional to using complete photosynthetic cells it is also possible to use the photosynthetically active organisms thereof, i.e. chloroplasts, and protoplasts from *Vaucheria litorea* are particularly preferred, and to preserve using the methods as described herein. It has been found that these protoplasts even in isolated form are able to survive for some time, i.e. up to some months, and to maintain their activity, i.e. they can deliver oxygen continuously outside the cell (Rumpho M E, Summer E J, Manhart J R. Solar-powered sea slugs. Mollusc/algal chloroplast symbiosis. Plant Physiol. 2000; 123: 29). Therefore, in one embodiment of the present invention these chloroplasts are contemplated to be preservable using the methods described herein.

Investigation of Photosynthetic Biomaterials in In Vivo Model

The preserved photosynthetic biomaterials may be validated on an in vivo model where safety and efficacy may be studied. Under general anesthesia, bilateral full skin defects may be created on the back of mice, and preserved photosynthetic scaffolds or controls (freshly prepared photosynthetic scaffolds and scaffolds without microalgae) may be implanted. Next, animals may be placed in individual cages equipped with LED lights in order to induce oxygen production of the scaffolds. At different time points after implantation, animals may be euthanized in order to evaluate the local and systemic effects of the implanted photosynthetic biomaterials. To do so, immune organs may be removed and analyzed, and whole blood may be collected in order to measure inflammatory cytokine concentrations in serum. Furthermore, regenerating tissue may be excised for the further analysis. Organs may be removed and whole blood collected. Harvested immune organs may be measured in size and weight and compared to total body weight, and further analyzed by histology and immunohistochemistry. Lymphocyte activation may be studied by fluorescence-activated cell sorting (FACS) analysis of splenic lymphocytes obtained from the homogenization of the harvested organ tissues. Serum may be separated from collected whole blood, and a cytokine beads assay may be performed to determine the concentration of inflammatory cytokines by a BD CBA Mouse Inflammation Kit (BD Pharmingen, NJ, USA). Regenerating tissue may be excised and analyzed by histology and immunohistochemistry. An inflammatory cytokine profile array on protein extracts obtained from the explanted scaffolds may be performed. RT-PCR analysis may be performed to detect microalgae mRNA in explanted scaffolds, which may be incubated in liquid TAP and further plated on TAP-agar plate to evaluate microalgae growth. Revascularization of the wound area upon implantation of photosynthetic biomaterials may be assessed by tissue transillumination and digital segmentation. All experiments and analysis would be compared to its control group, which includes non-preserved samples.

Thus, specific examples of methods of preserving photosynthetic cells and biomaterials have been disclosed. It should be apparent, however, to those skilled in the art that many more modifications besides those already described are possible without departing from the inventive concepts herein. While examples and variations of the many aspects of the invention have been disclosed and described herein, such disclosure is provided for purposes of explanation and illustration only. Thus, various changes and modifications may be made without departing from the scope of the claims.

Reference throughout this specification to "an embodiment" or "an implementation" means that a particular feature, structure, or characteristic described in connection with the embodiment is included in at least one embodiment or implementation. Thus, appearances of the phrases "in an embodiment" in various places throughout this specification are not necessarily all referring to the same embodiment or a single exclusive embodiment. Furthermore, the particular features, structures, or characteristics described herein may be combined in any suitable manner in one or more embodiments or one or more implementations.

Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

The word "exemplary" is used herein to mean "serving as an example, instance, or illustration." Any aspect described herein as "exemplary" is not necessarily to be construed as preferred or advantageous over other aspects. Unless specifically stated otherwise, the term "some" refers to one or more.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

As used in the description herein and throughout the claims that follow, the meaning of "a," "an," and "the" includes plural reference unless the context clearly dictates otherwise.

Combinations such as "at least one of A, B, or C," "one or more of A, B, or C," "at least one of A, B, and C," "one or more of A, B, and C," and "A, B, C, or any combination thereof" include any combination of A, B, and/or C, and may include multiples of A, multiples of B, or multiples of C. Specifically, combinations such as "at least one of A, B, or C," "one or more of A, B, or C," "at least one of A, B, and C," "one or more of A, B, and C," and "A, B, C, or any combination thereof" may be A only, B only, C only, A and B, A and C, B and C, or A and B and C, where any such combinations may contain one or more member or members of A, B, or C.

All structural and functional equivalents to the components of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

What is claimed is:

1. A preserved photosynthetic scaffold, comprising:
photosynthetically active cells seeded onto a biomaterial; and
wherein the photosynthetically active cells have been stored at temperatures between 1-5° C. without light for a period of at least 4 weeks.

2. The preserved photosynthetic scaffold of claim 1, wherein the photosynthetically active cells have been suspended in a nitrogen-containing medium under illumination after being stored at temperatures between 1-5° C. without light for the period of at least 4 weeks.

3. The preserved photosynthetic scaffold of claim 1, wherein the photosynthetically cells have been stored at temperatures between 1-5° C. without light for a period of at least 4 weeks prior to being seeded onto the biomaterial.

4. The preserved photosynthetic scaffold of claim 1, wherein the photosynthetically active cells comprise at least one of genetically engineered cells and isolated chloroplasts from *Chlamydomonas reinhardtii.*

5. The preserved photosynthetic scaffold of claim 1, wherein the period of at least 4 weeks is continuous.

* * * * *